(12) United States Patent
Allsop

(10) Patent No.: US 9,132,247 B2
(45) Date of Patent: Sep. 15, 2015

(54) DOSE INDICATOR DEVICE

(75) Inventor: Paul Allsop, Norfolk (GB)

(73) Assignee: CONSORT MEDICAL PLC, Hemel Hempstead (GB)

(*) Notice: Subject to any disclaimer, the term of this patent is extended or adjusted under 35 U.S.C. 154(b) by 538 days.

(21) Appl. No.: 13/487,791

(22) Filed: Jun. 4, 2012

(65) Prior Publication Data

US 2012/0312301 A1     Dec. 13, 2012

(30) Foreign Application Priority Data

Jun. 8, 2011 (GB) .................................. 1109569.2

(51) Int. Cl.
*A61M 15/00*     (2006.01)

(52) U.S. Cl.
CPC ......... *A61M 15/009* (2013.01); *A61M 15/0075* (2014.02); *A61M 15/0071* (2014.02)

(58) Field of Classification Search
CPC .......... A61M 15/009; A61M 15/0068; A61M 15/0071; A61M 15/0073; A61M 15/0075; A61M 15/0076; A61M 15/0078; G06M 1/04; G06M 1/041; G06M 1/083; G06M 1/163
USPC ............. 128/200.11, 200.12, 200.13, 200.14, 128/200.15, 200.16, 200.17, 200.18, 128/200.19, 200.21, 200.22, 200.23, 128/200.24, 203.12, 203.15, 205.23
See application file for complete search history.

(56) References Cited

U.S. PATENT DOCUMENTS

| | | | |
|---|---|---|---|
| 6,155,251 A | 12/2000 | Hauser | |
| 6,283,365 B1 * | 9/2001 | Bason | 235/116 |
| 7,780,038 B2 | 8/2010 | Ingram et al. | |
| 2003/0178020 A1 | 9/2003 | Scarrott | |
| 2005/0087191 A1 | 4/2005 | Morton et al. | |
| 2007/0240708 A1 * | 10/2007 | Schuckmann | 128/200.14 |

(Continued)

FOREIGN PATENT DOCUMENTS

| | | |
|---|---|---|
| CN | 101099170 | 1/2008 |
| EP | 0 775 499 A2 | 5/1997 |

(Continued)

OTHER PUBLICATIONS

Combined Search and Examination Report under Section 17 for GB 1109569.2 dated Sep. 29, 2011.

(Continued)

*Primary Examiner* — Lynne Anderson
*Assistant Examiner* — Elliot S Ruddie
(74) *Attorney, Agent, or Firm* — Smith, Gambrell & Russell, LLP

(57) ABSTRACT

Dose indicator device for metered dose inhalers having a base, inner wheel, outer wheel, drive, transmission cog and flexible cover. The drive, inner wheel and outer wheel are concentrically, rotatably mounted about a first rotation axis. The cog rotates about a second axis parallel to the first. The inner wheel has inner annular surface primary indexing teeth and one or more outer annular surface secondary indexing teeth. The outer wheel has indexing teeth on an inner annular surface. The cog has gear teeth engageable with outer wheel indexing teeth and engageable by one or more inner wheel secondary indexing teeth. The drive has one or more arms engageable with primary indexing teeth. The flexible cover being flexible downwardly wherein, in use, downward drive movement is accompanied by drive rotation about the first axis, the rotation causing inner wheel rotation by interengagement of the drive and the primary indexing teeth.

16 Claims, 6 Drawing Sheets

(56) References Cited

U.S. PATENT DOCUMENTS

| | | |
|---|---|---|
| 2007/0284383 A1 | 12/2007 | Wright et al. |
| 2010/0212664 A1 | 8/2010 | Bishop et al. |
| 2012/0012106 A1 | 1/2012 | Bari |
| 2012/0103331 A1 | 5/2012 | Laut et al. |

FOREIGN PATENT DOCUMENTS

| | | |
|---|---|---|
| EP | 1 758 631 B1 | 2/2010 |
| GB | 2 288 259 A | 10/1995 |
| GB | 2 448 838 A | 10/2008 |
| GB | 2 469 068 A | 10/2010 |
| WO | 2004/089451 | 10/2004 |
| WO | 2010/125288 | 11/2010 |

OTHER PUBLICATIONS

English Translation of Chinese Office Action and Search Report for CN201210190370.7 dated Nov. 3, 2014.

* cited by examiner ated metered dose inhaler. devices, and in particular to a
DOSE INDICATOR DEVICE The present disclosure relates to a dose indicator device and apparatus comprising such devices, and in particular to a dose indicator device for use with, or incorporated as part of a pressurised metered dose inhaler.

BACKGROUND

It has been recognised that there is a need to provide accurate information to a user of a dispensing apparatus, such as a pressurised metered dose inhaler, concerning the quantity of doses delivered from, or remaining in, the dispensing apparatus. Without such information, there is a danger that a user may be unaware that the dispensing container of the dispensing apparatus is empty or close to empty. This is especially dangerous where the dispensing apparatus is for use in delivering medicinal compounds for the treatment of chronic or acute symptoms, for example, as in the case of a pressurised metered dose inhaler used for treating asthmatic reactions.

It is known to provide a dispensing apparatus with a dose indicator device. Typically such dose indicator devices are triggered by movement of the dispensing container wherein the movement either directly or indirectly provides the motive force for incrementing or decrementing the dose indicator device. EP1758631 disclose one example of a dose indicator device. This device, while accurate and robust, comprises a relatively large number of separate components.

Often a dose indicator device is arranged such that once attached to an apparatus it cannot be separated therefrom. This provides a level of reassurance to a user that the indicator is accurate since, once the indicator is attached to the apparatus, the indicator can only increment when a dose is dispensed from the associated apparatus.

It would be desirable to produce a dose indicator device that requires fewer components.

SUMMARY OF THE DISCLOSURE

According to the present disclosure there is provided a dose indicator device for a pressurised metered dose inhaler comprising:

a base suitable for mounting to an upper end of a dispensing container of a pressurised metered dose inhaler, an annular inner wheel, an annular outer wheel, a drive member, a transmission cog and a flexible cover;

the drive member, annular inner wheel and annular outer wheel being concentrically mounted on the base to be rotatable about a first axis of rotation;

the transmission cog being mounted on the base between the annular inner wheel and the annular outer wheel to be rotatable about a second axis of rotation parallel to the first axis of rotation;

the annular inner wheel comprising a plurality of primary indexing teeth on an inner annular surface thereof and one or more secondary indexing teeth on an outer annular surface thereof;

the annular outer wheel comprising a plurality of indexing teeth on an inner annular surface thereof;

the transmission cog comprising a plurality of gear teeth on an outer annular face thereof which, in use, can engage the indexing teeth of the annular outer wheel and which can also be engaged by the one or more secondary indexing teeth of the annular inner wheel;

the drive member being mounted within the annular inner wheel;

the drive member comprising a body having one or more drive arms which, in use, can engage the primary indexing teeth of the annular inner wheel;

the flexible cover being flexible downwardly wherein, in use, downward movement of the drive member is accompanied by rotation of the drive member about the first axis of rotation; said rotation causing rotation of the annular inner wheel by interengagement of the drive arms of the drive member and the primary indexing teeth of the annular inner wheel.

Advantageously, the dose indicator device comprises a relatively small number of separate components and is suitable to form a compact, space-saving design.

In a first arrangement, the flexible cover and drive member may be interconnected such that downward movement of the flexible cover is accompanied by rotation of the drive member about the first axis of rotation.

The flexible cover may comprise, or be coupled to, one part of a cam and follower mechanism and the drive member may comprise, or be coupled to, another part of the cam and follower mechanism.

In one example the follower of the cam and follower mechanism is one or more pegs and the cam of the cam and follower mechanism is a cam surface provided by one or more slots that slidingly receive the one or more pegs.

The flexible cover may have an inherent memory which causes the flexible cover to return to its inherent shape in the absence of a force.

A lower end of the drive body of the drive member which contacts a central boss of the base may be dome-shaped. By dome-shaped is meant that the lower end of the drive body is part-spherical, rounded or otherwise shaped so as to reduce the area of contact between the drive body and the base. This helps to reduce the level of friction between the components which otherwise might prevent rotation of the drive member about the first axis of rotation. Preferably the lower end is part-spherical in shape.

In a second arrangement, the drive member may comprise a biasing mechanism. The biasing mechanism of the drive member may be a coil spring. Alternatively, the biasing mechanism of the drive member may comprise a plurality of flexible legs depending from the drive member body which are orientated relative to the first axis of rotation such that movement of the drive member body along the first axis of rotation causes twisting of the drive member body about the first axis of rotation. In both cases a mechanism is provided which functionally serves to cause the drive member to rotate about the first axis of rotation as the drive member moves along the first axis of rotation. Thus, depression of the flexible cover, and hence the drive member, can be used to cause rotation of the annular inner wheel and, after a predetermined number of actuations, rotation of the transmission cog and annular outer wheel.

An upper end of the drive member which contacts the flexible cover may be dome-shaped. By dome-shaped is meant that the upper end of the drive member is part-spherical, rounded or otherwise shaped so as to reduce the area of contact between the drive member and the flexible cover. This helps to reduce the level of friction between the components which otherwise might prevent rotation of the drive member about the first axis of rotation. Preferably the upper end is part-spherical in shape.

For all of the arrangements, the base may comprise a first ratchet mechanism for engagement with the annular inner wheel and a second ratchet mechanism for engagement with the annular outer wheel.

The ratchet mechanisms advantageously serve to restrain movement of the annular inner wheel and annular outer wheel other than when the wheels are being positively driven during a counting action. This helps to minimise the chances of the dose indicator device changing the displayed indication if the device is dropped, shaken or otherwise knocked.

The annular inner wheel, the transmission cog and the annular outer wheel may have a gear ratio such that for every 10 incremental rotations of the annular inner wheel the annular outer wheel is incrementally rotated once.

The intermittent engagement of the one or more secondary indexing teeth of the annular inner wheel and the gear teeth of the transmission cog serve to enable the annular outer wheel to be incremented only after a plurality of rotational increments of the inner wheel. For example, the inner wheel and the annular outer wheel may have a gear ratio of 10:1 such that for every 10 incremental rotations of the inner wheel the annular outer wheel is incrementally rotated once. This can be achieved by providing a single secondary indexing tooth and 10 primary indexing teeth on the inner wheel. Consequently, for every 10 actuations of the inner wheel (as a result of downward movement of the flexible cover) the inner wheel will rotate through 360° and the secondary indexing tooth will, via engagement with the gear teeth of the transmission cog and rotation of the transmission cog by one increment, cause the annular outer wheel to rotate one increment.

In another example, a gear ratio of 10:1 can be achieved by providing two secondary indexing teeth on the inner wheel at 180° spacing and 20 primary indexing teeth. Other gear ratios can be used as desired. For example, the annular outer wheel can be arranged to incrementally rotate every 20 actuations of the pressurised dispensing container by providing one secondary indexing tooth and 20 primary indexing teeth on the inner wheel.

The total number of dosages that can be counted by the dose indicator device can be altered by altering the number of indexing teeth on the annular outer wheel as well as the number of primary indexing teeth on the inner wheel. For example, a total count of 200 can be achieved by providing 10 primary indexing teeth and one secondary indexing tooth on the inner wheel and 21 indexing teeth on the annular outer wheel.

The dose indicator device may further comprise a cover having a window; wherein a planar face of the annular outer wheel orientated perpendicularly to the second axis of rotation may be provided with a plurality of dosage indicia which are viewable through the window.

The dosage indicia may be in the form of numbers, words, letters, colours, pictograms or similar. For example a decreasing series of numbers can be displayed: 200, 190, 180, 170 where a gear ratio of 10:1 is used between the inner wheel and the outer annular wheel. Alternatively, where it is not desired to show a numerical count but simply to indicate to a user that the end of the useful life of the pressurised metered dose inhaler is approaching, the indicia could be in the form of a changing colour, e.g. a display that changes from green, through orange to red, or in the form of words which are displayed near or at the end of the pack life such as "Order replacement now" and "Empty".

Dosage indicia may be presented only on the annular outer wheel where individual dosage counts are not to be displayed to a user. Alternatively, the inner wheel may also be provided with dosage indicia where individual dosage counts are desired to be displayed.

The window of the dose indicator device may be sized so as only to show the annular outer wheel and to obscure view of the inner wheel. In this way a user of the device will only see the indication change when the outer annular wheel rotates. Alternatively, the window may allow both the inner wheel and the annular outer wheel to be visible. This may be desired where the dose indicator device is to indicate individual counts.

The dose indicator device may comprise only six component parts.

The present disclosure also relates to a pressurised metered dose inhaler comprising a dose indicator as described above.

The components of the dose indicator device are preferably formed from plastics mouldings, except for the compression spring (when present) which may be metal or plastic.

Rigid components of the dose indicator device may be formed from, for example, polyester, nylon, polypropylene, acetal or similar.

Preferably, the restraining member and actuator member are formed from an elastic material such that imparted strains during normal actuation are recoverable elastically.

The dose indicator device may be used with, or form a part of a pharmaceutical dispensing device, such as, for example, a pulmonary, nasal, or sub-lingual delivery device. A preferred use of the dose indicator device is with a pharmaceutical pressurised metered dose aerosol inhaler device. The term pharmaceutical, as used herein, is intended to encompass any pharmaceutical, compound, composition, medicament, agent or product which can be delivered or administered to a human being or animal, for example pharmaceuticals, drugs, biological and medicinal products. Examples include antiallergics, analgesics, bronchodilators, antihistamines, therapeutic proteins and peptides, antitussives, anginal preparations, antibiotics, anti-inflammatory preparations, hormones, or sulfonamides, such as, for example, a vasoconstrictive amine, an enzyme, an alkaloid, or a steroid, including combinations of two or more thereof. In particular, examples include isoproterenol [alpha-(isopropylaminomethyl)protocatechuyl alcohol], phenylephrine, phenylpropanolamine, glucagon, adrenochrome, trypsin, epinephrine, ephedrine, narcotine, codeine, atropine, heparin, morphine, dihydromorphinone, ergotamine, scopolamine, methapyrilene, cyanocobalamin, terbutaline, rimiterol, salbutamol, flunisolide, colchicine, pirbuterol, beclomethasone, orciprenaline, fentanyl, and diamorphine, streptomycin, penicillin, procaine penicillin, tetracycline, chlorotetracycline and hydroxytetracycline, adrenocorticotropic hormone and adrenocortical hormones, such as cortisone, hydrocortisone, hydrocortisone acetate and prednisolone, insulin, cromolyn sodium, and mometasone, including combinations of two or more thereof.

The pharmaceutical may be used as either the free base or as one or more salts conventional in the art, such as, for example, acetate, benzenesulphonate, benzoate, bicarbonate, bitartrate, bromide, calcium edetate, camsylate, carbonate, chloride, citrate, dihydrochloride, edetate, edisylate, estolate, esylate, fumarate, fluceptate, gluconate, glutamate, glycollylarsanilate, hexylresorcinate, hydrobromide, hydrochloride, hydroxynaphthoate, iodide, isethionate, lactate, lactobionate, malate, maleate, mandelate, mesylate, methylbromide, methylnitrate, methylsulphate, mucate, napsylate, nitrate, pamoate, (embonate), pantothenate, phosphate, diphosphate, polygalacturonate, salicylate, stearate, subacetate, succinate, sulphate, tannate, tartrate, and triethiodide, including combinations of two or more thereof. Cationic salts may also be used, for example the alkali metals, e.g. Na and K, and ammonium salts and salts of amines known in the art to be pharmaceutically acceptable, for example glycine, ethylene diamine, choline, diethanolamine, triethanolamine, octadecylamine, diethylamine, triethylamine, 1-amino-2-propanol-amino-2-

(hydroxymethyl)propane-1,3-diol, and 1-(3,4-dihydroxyphenyl)-2 isopropylaminoethanol.

The pharmaceutical will typically be one which is suitable for inhalation and may be provided in any suitable form for this purpose, for example as a solution or powder suspension in a solvent or carrier liquid, for example ethanol, or isopropyl alcohol. Typical propellants are HFA134a, HFA227 and dimethyl ether.

The pharmaceutical may, for example, be one which is suitable for the treatment of asthma. Examples include salbutamol, beclomethasone, salmeterol, fluticasone, formoterol, terbutaline, sodium chromoglycate, budesonide and flunisolide, and physiologically acceptable salts (for example salbutamol sulphate, salmeterol xinafoate, fluticasone propionate, beclomethasone dipropionate, and terbutaline sulphate), solvates and esters, including combinations of two or more thereof. Individual isomers such as, for example, R-salbutamol, may also be used. As will be appreciated, the pharmaceutical may comprise of one or more active ingredients, an example of which is flutiform, and may optionally be provided together with a suitable carrier, for example a liquid carrier. One or more surfactants may be included if desired.

BRIEF SUMMARY OF THE DRAWINGS

Embodiments of the present disclosure will now be described, by way of example, with reference to the accompanying drawings, in which: —

DETAILED DESCRIPTION

Figure 1:
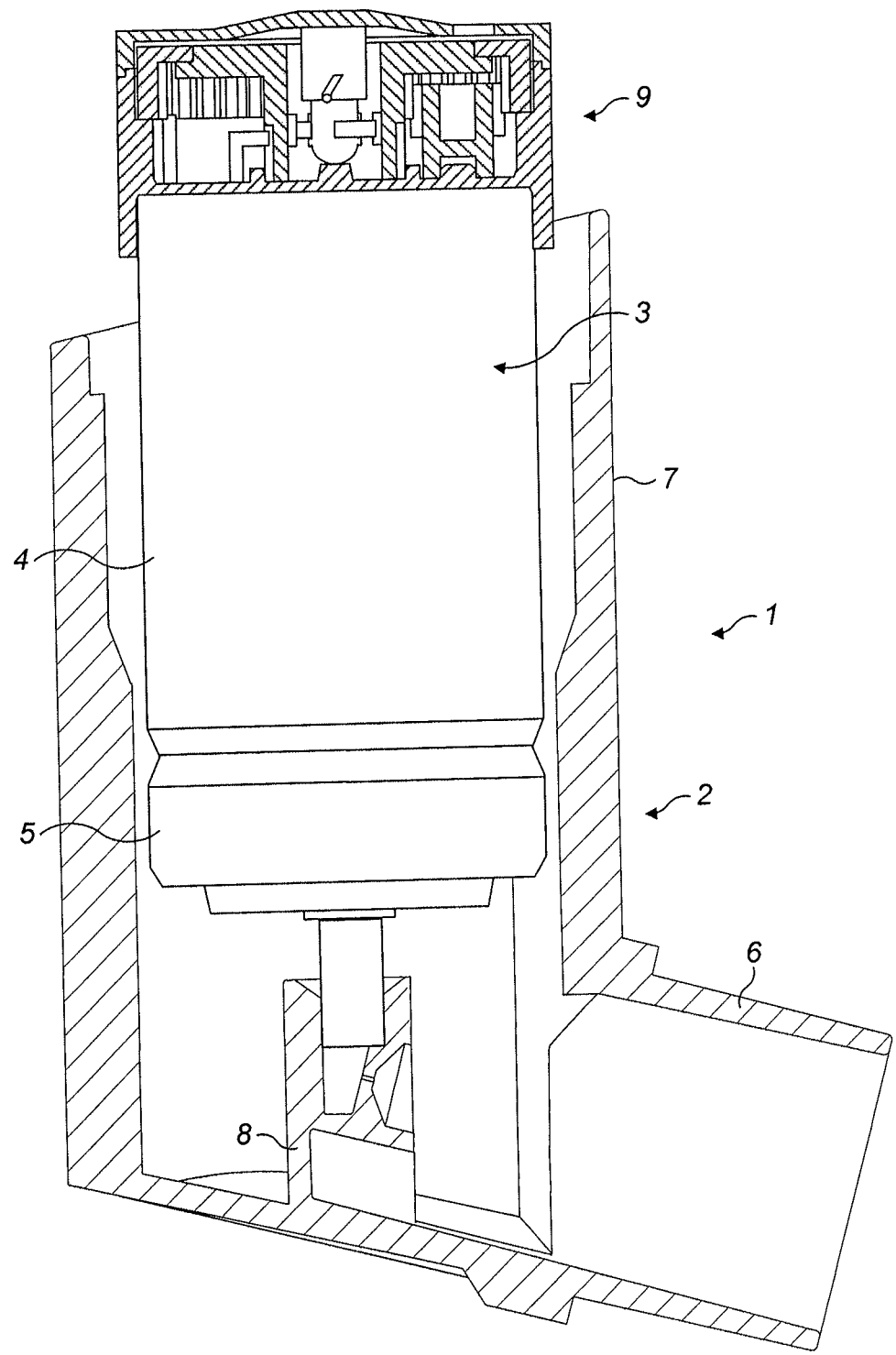
FIG. 1 is a part cross-sectional view of a first embodiment of a dose indicator device according to the present disclosure shown in context with a pressurised metered dose inhaler including a container.

FIG. 1 shows a cross-sectional view of a pressurised metered dose inhaler 1 which comprises a housing 2 that contains a pressurised dispensing container 3. The housing 2 comprises a generally tubular body 7 and a depending mouthpiece 6 at one end. The tubular body 7 may have a generally circular cross-sectional shape. However, the tubular body may alternatively comprise a squarer cross-sectional shape with a front wall, side walls and rear wall. A stem block 8 is provided at a basal end of the tubular body 7 nearest the mouthpiece 6. The pressurised dispensing container 3 typically comprises a canister 4 and a valve 5 which is shown schematically. To assemble the pressurised metered dose inhaler, the dispensing container 3 is inserted into the tubular body 7 of the housing 2 such that a valve stem of the valve 5 is received in the stem block 8. According to the present disclosure, the pressurised metered dose inhaler 1 includes a dose indicator device marked generally by reference 9. The dose indicator device 9 is located towards at an end of the container 3 opposite the valve 5.

In the following description, unless the context otherwise requires, the term "inwardly-facing" refers to a direction which is inwards towards a central axis of the dispensing container 3 within the tubular body 7 or inwards towards a central axis of the dose indicator device 9 such as the dose indicator device 9 would be oriented when attached, in use, to the container 3, whether or not the dose indicator device 9 is in fact attached to the container 3. The term "outwardly-facing" refers to a direction which is outwards away from the pressurised dispensing container 3 within the tubular body 7 or away from the central axis of the dose indicator 9.

Further, terms such as "upwards" refer to a direction which is towards the end opposite the valve 5 while terms such as "downwards" refer to a direction which is towards the end at which the valve 5 is located. Similarly, in the context of the dose indicator device, terms such as "upwards" refer to the end of the dose indicator 9 which would be furthest from the valve end of the container 3 when the indicator 9 is, in use, attached to a container 3 for use in an inhaler 1. Similarly, terms such as "downwards" refer to an opposite direction.

In general, the dose indicator device 9 comprises a base 14 suitable for mounting to an upper end of a dispensing container 3 of a pressurised metered dose inhaler 1. The dose indicator 9 also comprises an annular inner wheel 11, an annular outer wheel 12, a drive member 13, a transmission cog 17 and a flexible cover 16.

Figure 2:
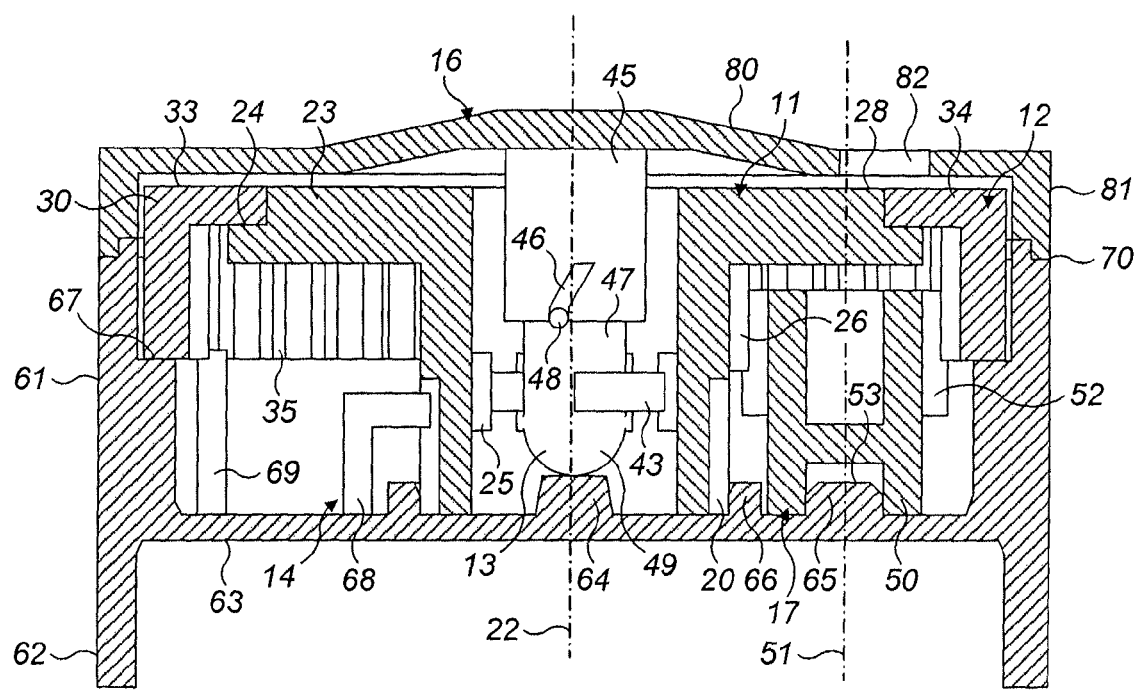
FIG. 2 is an enlarged part cross-sectional view of the first embodiment of the dose indicator as illustrated in FIG. 1.
Figure 3:
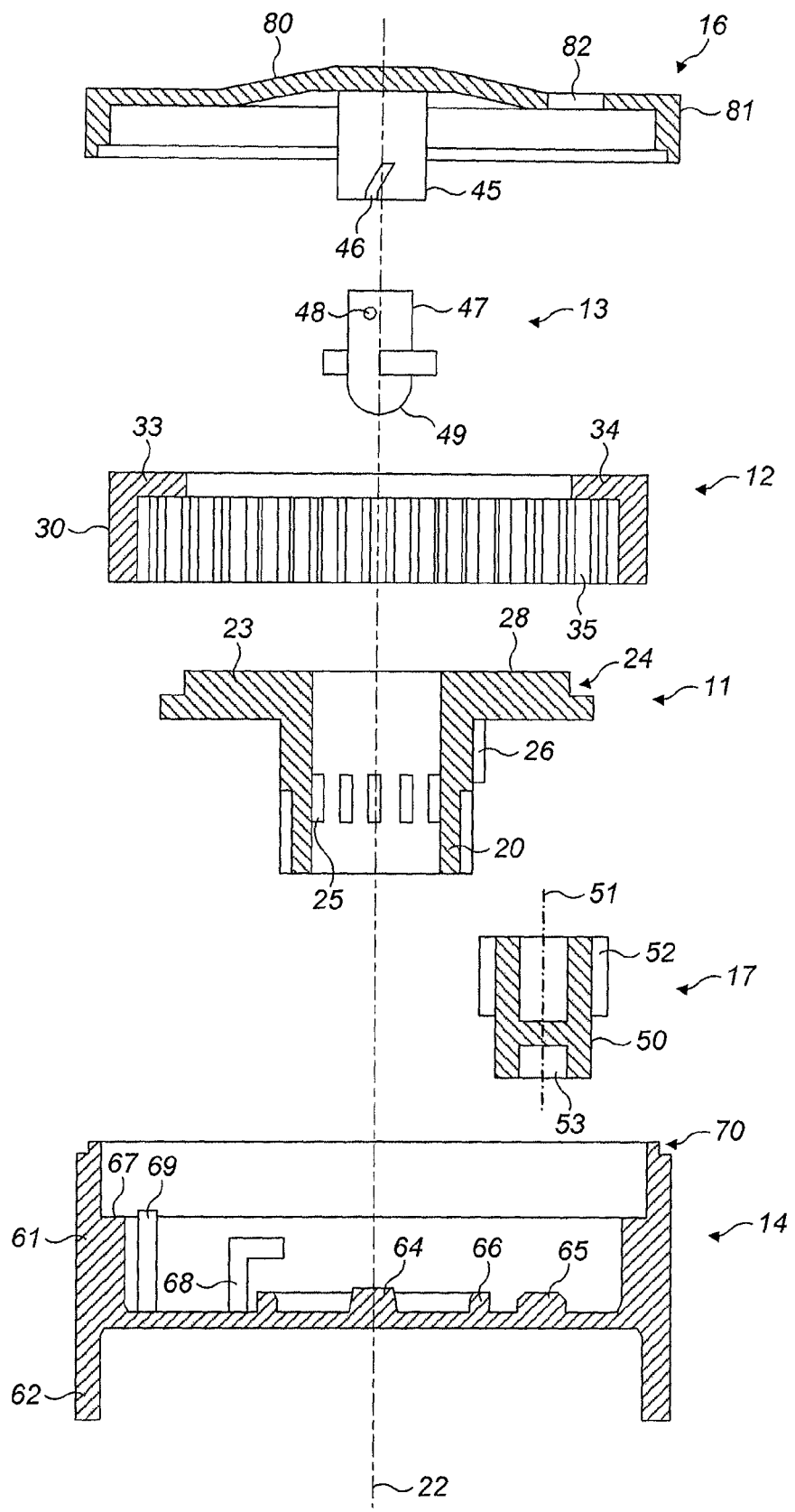
FIG. 3 is an exploded part cross-sectional view of the dose indicator device of FIG. 2.

As shown in FIGS. 2 and 3, the inner wheel 11 comprises a cylindrical body 20, having a cylindrical axis. The cylindrical body 20 is mounted, in use, to rotate on its cylindrical axis about a first rotational axis 22, as marked on FIG. 2. The inner wheel 11 further comprises an annular flange 23 having an upper surface 28 which is orthogonal to the first rotational axis 22. The annular flange 23 comprises a circumferential recess 24 in its upper surface 28.

The cylindrical body 20 is further provided with two sets of formations which are arranged circumferentially around the body 20. The first set of formations is a plurality of primary indexing teeth 25 positioned on an inner surface of the inner wheel 11. In the example shown there are 10 primary indexing teeth 25. The second set of formations is in the form of a single secondary indexing tooth 26 positioned on an outer surface of the inner wheel 11.

The transmission cog 17 comprises a cylindrical body 50, having a cylindrical axis. At the lower end of the cylindrical body 50 is a lower recess 53. The cylindrical body is mounted, in use, to rotate on its cylindrical axis about a second rotational axis 51 as marked on FIG. 2. The body 50 is provided with one or more gear teeth 52 on its outer cylindrical face. The one or more gear teeth 52 are arranged to cooperate with the secondary indexing tooth 26 of the inner wheel 11 such that, on rotation of the inner wheel 11, the secondary indexing tooth 26 of the inner wheel 11 engages with one of the one or more gear teeth 52 of the transmission cog 17 to cause rotation of the transmission cog 17.

The annular outer wheel 12 has a generally cylindrical body 30, having a cylindrical axis. The cylindrical axis of the cylindrical body 30 is coaxial with the first axis of rotation 22, as marked on FIG. 2. In use, the generally cylindrical body 30 is rotatable about the first axis of rotation 22. At an upper end of the cylindrical body is an annular flange 33 in a plane orthogonal to the first axis of rotation 22. The annular flange 33 has an upper surface 34 which is in a same plane as the upper surface 28 of the inner wheel 11. The annular flange 33 of the outer wheel 12 is at least partly located within the circumferential recess 24 of the annular flange 23 of the inner wheel 11.

One or more indexing teeth 35 are arranged on an inner annular surface of the annular body 30. The one or more indexing teeth 35 are arranged to cooperate with the one or more gear teeth 52 of the transmission cog 17 such that, on rotation of the transmission cog 17, the one or more gear teeth 52 of the transmission cog 17 engage with the one or more indexing teeth 35 of the annular outer wheel 12 to cause rotation of the annular outer wheel 12.

The drive member 13 comprises a cylindrical body 47, a pair of pegs 48 and a pair of drive arms 43. The pegs 48 extend radially beyond the circumference of the cylindrical body perpendicularly to the axis 22. The two drive arms 43 extend from the body 47 and are arranged to cooperate, in use, with the inner indexing teeth 25 of the inner annular wheel 11. The cylindrical body 47 further comprises a domed lower end 49.

The flexible cover 16 is made of a material having an inherent memory such that, once a deforming force is removed, the cover 16 naturally and automatically returns to its original shape. The flexible cover 16 comprises a flexible plate 80, a rim 81 and a window 82 through which, when the dose indicator device 9 is assembled, a portion of the upper surface of one or both of the annular flanges 28, 34 may be viewed. The window 82 may simply be an aperture which may or may not also include a transparent material. Attached to the underside of the flexible plate 80 of the flexible cover 16 is a cylindrical extension 45 which when assembled engages with the drive member 13. The cylindrical extension 45 comprises a cylindrical sleeve having two slots 46 therein which extend upwardly from the free end of the cylindrical extension part way along the length of the extension 45. Each slot 46 is set in a direction having a longitudinal directional element (parallel with the axis of the cylindrical extension 45) and a simultaneous circumferential directional element (around the circumference of the cylindrical extension 45) such that movement of the peg within the slot causes the drive member 13 to rotate as the cylindrical extension 45 moves down with respect to the drive member 13.

As shown in FIG. 2, on assembly the upper end of the body 47 of the drive member 13 is received in the open lower end of the cylindrical extension 45 with each peg 48 being slidingly received in one of the slots 46. The angling of the slots 46 to the axis 22 means that as the cylindrical extension 45 is moved along its cylindrical axis with respect to the body 47, each peg 48 slides along its respective slot 46 causing the drive member 13 to rotate on its cylindrical axis 22. Thus, the slots 46 provide a pair of cam surfaces and the pegs 48 a pair of cam followers.

The body 47 and extension 45 need not be cylindrical. They may take any shape which allows them to move coaxially relative to one another such that the axial movement of the one with respect to the other causes the drive member 13 to rotate as a consequence of the peg and slot arrangement. In addition, while the cylindrical extension 45 is, in the illustrated embodiment, outside the body 47, this may be reversed.

Referring to FIG. 3, the base 14 comprises an upwardly projecting rim 61, a downwardly projecting rim 62, a transverse plate 63, a central boss 64, an offset boss 65, an annular formation 66, an annular ledge 67, a first pawl 68 and a second pawl 69.

The downwardly projecting rim 62 is such as to provide a cylindrical recess at the base of the dose indicator device 9 by which the dose indicator device 9 may be attached to the cylindrical end of the container 3.

The offset boss 65 is dimensioned to cooperate with the lower recess 53 of the transmission cog 17 such that the transmission cog is rotatable on its cylindrical axis about the offset boss 65.

When the dose indicator device 9 is assembled, the annular inner wheel 11, annular outer wheel 12, drive member 13 and transmission cog 17 are enclosed between the base 14 and the flexible cover 16. Attachment of the cover 16 retains the components of the dose indicator device 9.

The dose indicator device 9 may be assembled as follows. First, the transmission cog 17 is positioned with respect to the base 14 such that the lower recess 53 of the transmission cog 17 cooperates with the offset boss 65. Secondly, the inner annular wheel 11 is placed with respect to the base such that a lower end of the wheel 11 sits within the annular formation 66 and with the upper surface of the inner wheel 11 facing upwards.

As shown in FIG. 2, the first rotational axis 22 of the inner wheel 11 is parallel and offset from the second rotational axis 51 of the transmission cog 17.

Next, the outer annular wheel 12 is placed coaxially with respect to the inner annular wheel 11 such that a lower edge of the cylindrical body 30 rests on the annular ledge 67 of the base 14. In addition, an innermost part of the annular flange 33 is within the circumferential recess 24 of the inner wheel 11 and such that the upper surface 34 of the annular flange 33 of the outer wheel 12 is in the same plane as the upper surface 28 of the annular flange 23 of the inner wheel 11.

The flexible cover 16, having the cylindrical extension 45 as part thereof, is placed over the base 14 while the cylindrical body 47 of the drive member 13 is in between the extension 45 and the base 14 (accessible through the annular opening at the centre of the inner and outer wheels). The flexible cover 16 is pushed towards the base 14 such that the two pegs 48 of the body 47 of the drive member 13 sit within an entrance to each slot 46 and such that the domed end 49 of the body 47 abuts the central boss 64 of the base 14. The upper end of the upwardly extending rim 61 of the base 14 is shaped to provide a snap fit 70 with the downwardly facing rim 81 of the flexible cover 16.

Preferably, the rim 81 and/or rim 61 are provided with formations to ensure correct alignment of the window 82 on fitting of the cover 16.

Once the dose indicator device 9 is assembled, the upper surface of one or both annular flanges 28, 34 are viewable through the window 82. The upper surfaces 28, 34 may be provided with one or more indicia to provide information to a user of the pressurised metered dose inhaler 1 regarding the number of doses dispensed from the inhaler or remaining in the inhaler. For example, the indicia may comprise a set of increasing or decreasing numbers, a series of pictograms, a series of words or a band of changing colour —e.g. a band which changes from green to red around the upper surface of one or both of the annular flanges 28, 34.

Once the dose indicator device 9 has been assembled it can be attached to a container 3 housed in a housing 7 of a metered dose inhaler, as illustrated in FIG. 1.

Attachment of the dose indicator device 9 to the container 3 may be my means of a push fit, perhaps with a highly toleranced mutually-engaging formation and/or with adhesive.

Operation of the metered dose inhaler 1 will now be described. In a normal metered dose inhaler 1 without any dose indicator device 9, the dispensing container 3 is depressed relative to the housing 2 such that the canister 4 moves downwardly within tubular body 7 towards the stem block 8 to actuate the valve.

In the case of a metered dose inhaler 1 having a dose indicator device 9 of the present disclosure, the user depresses the container 3 with respect to the housing 2 by depressing the dose indicator device 9.

Depression of the flexible plate 80 of the flexible cover 16 causes the cylindrical extension 45 also to move downwards which in turn causes the cylindrical body 47 of the drive member 13 to rotate in a first direction by virtue of the followers in the form of the pegs 48 moving along the cam surfaces formed by the slots 46.

As the drive member 13 rotates, the drive arms 43 also rotate. Since the drive arms 43 are arranged to cooperate with the primary indexing teeth of the inner wheel 11, rotation of the drive arms 43 causes the inner wheel 11 to rotate in the first direction.

The lower end of the cylindrical body 47 of the drive member 13 being domed reduces friction which might provide resistance to rotation. Other non-domed alternatives are contemplated within the scope of the claims.

Once the pegs 48 reach the end of the slots 46, further depression of the flexible plate 80 causes the entire dose indicator device 9 to move downwards which, in turn, causes the container 3 to move downwards such that the valve stem, retained within the stem block 8, moves relative to the container in order cause actuation of the device such that a dose is dispensed from the container 3.

Once the dose has been dispensed, the user ceases to depress the flexible plate 80 which causes the container to move upwards by virtue of a biasing means in the valve stem. Furthermore, the flexible plate 80 of the dose indicator device 9 returns to its original position. This means that the cylindrical extension 45 moves upwards with respect to the body 47 of the drive member 13. Consequently, the pegs 48 slide back down the slots 46 such that the body 47 rotates in a second direction (opposite to the first direction) with respect to the cylindrical extension 45. The first pawl 68 acts as a ratchet to prevent the first wheel 11 from rotating in the second direction despite the cylindrical body 47 of the drive member 13 moving in the second direction. The drive arms 43 are sufficiently flexible so that they flex to ride over the primary indexing teeth 25 on rotation in the second direction but immediately spring back to their original shape once having passed the primary indexing teeth 25.

Consequently, for every depression of the flexible plate 80, a dose is dispensed from the container 3 and the inner wheel 11 is caused to rotate by one primary indexing tooth 25.

In the specific example, the inner wheel 11 comprises 10 primary indexing teeth 25 and one secondary indexing tooth 26. Thus, the inner wheel 11 will make one full rotation for every 10 actuations (i.e. depressions of the flexible cover 16).

Further, in the specific example, the inner wheel 11 comprises one secondary indexing tooth 26. For every full rotation of the inner wheel 11, the secondary indexing tooth 26 will once come into contact with one of the gear teeth 52 of the transmission cog 17. Contact of the secondary indexing tooth 26 with a first of the gear teeth 52 will cause the transmission cog 17 to rotate. At the same time, a second of the gear teeth 52, opposite the first gear tooth 52, will engage with an indexing tooth 35 of the outer wheel 12 which will cause the outer wheel to rotate one increment.

A second pawl 69 acts to prevent rotation of the outer wheel 12 without rotation of the transmission cog 17. Rotation of the outer wheel as a consequence of rotation of the transmission cog provides sufficient force for the pawl to bend to allow rotation of the outer wheel 12. This feature provides protection against the risk that the outer wheel will rotate unintentionally, such as when the device is dropped.

Since in the illustrated example there are 10 primary indexing teeth 25 on the inner wheel 11 for every one secondary indexing tooth 26, the transmission cog 17 will rotate one increment for every full rotation of the inner wheel 11. Furthermore, since the teeth on the transmission cog 17 are arranged such as to interlock with the indexing teeth on the outer wheel 12, the outer wheel 12 will also rotate by one tooth 35 for every complete revolution of the inner wheel 11. As such, the upper surface 34 of the annular flange 33 of the outer wheel 12 is used to display tens while the upper surface 28 of the inner wheel 11 is used to display units. In other words, the combination of the upper surfaces 34, 28 when viewed through the window 82 appear to count down from, say, 200 to 00 (or count up from 0 to 200).

Alternatively, the viewing window 82 may be of reduced size and only show to a user the upper surface 34 of the annular flange 33 of the outer wheel 12 (and not the upper surface 28 of the annular flange 23 of the inner wheel 11). In such a situation the dose indicator device 9 would only change its display as read by the user each time the inner wheel 11 completes a full rotation.

The gear ratio between the inner wheel 11 and the outer wheel 12 can be adjusted by varying the number of primary indexing teeth 25, secondary indexing teeth (or tooth) 26, transmission cog gear teeth 52 and indexing teeth 35 on the outer wheel 12.

Alternative embodiments of the disclosure will now be described, to the extent that they differ from the first embodiment as already explained.

Figure 4:
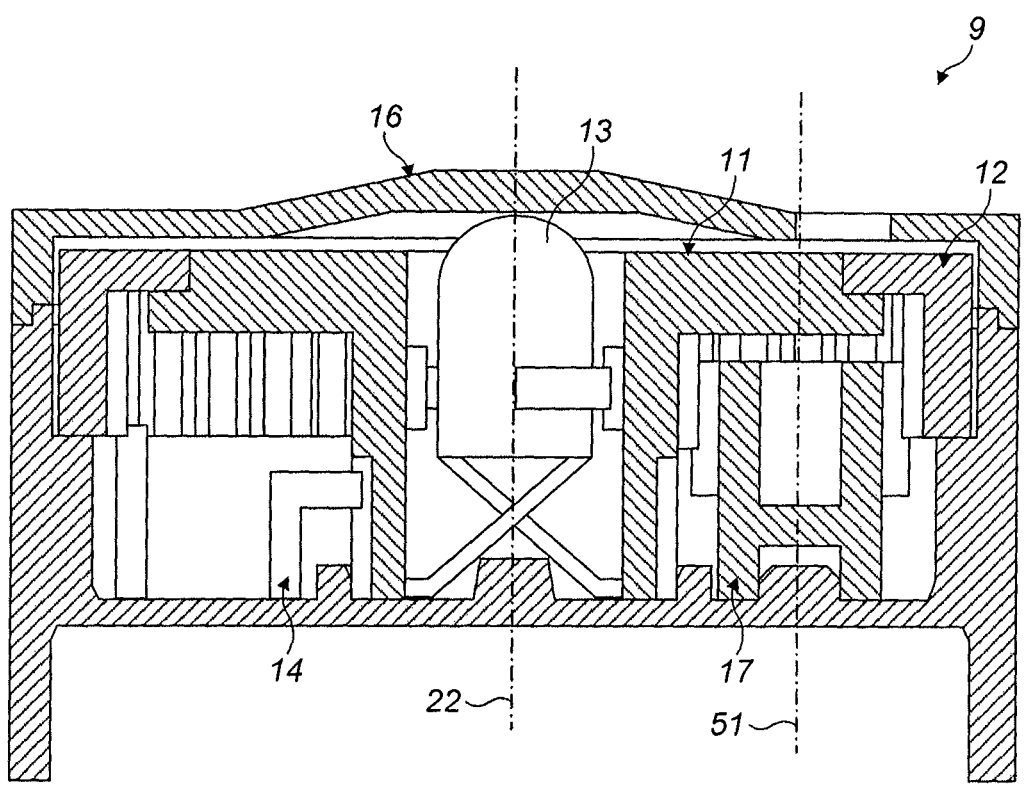
FIG. 4 is a part cross-sectional view of a second embodiment of a dose indicator device according to the present disclosure.
Figure 5:
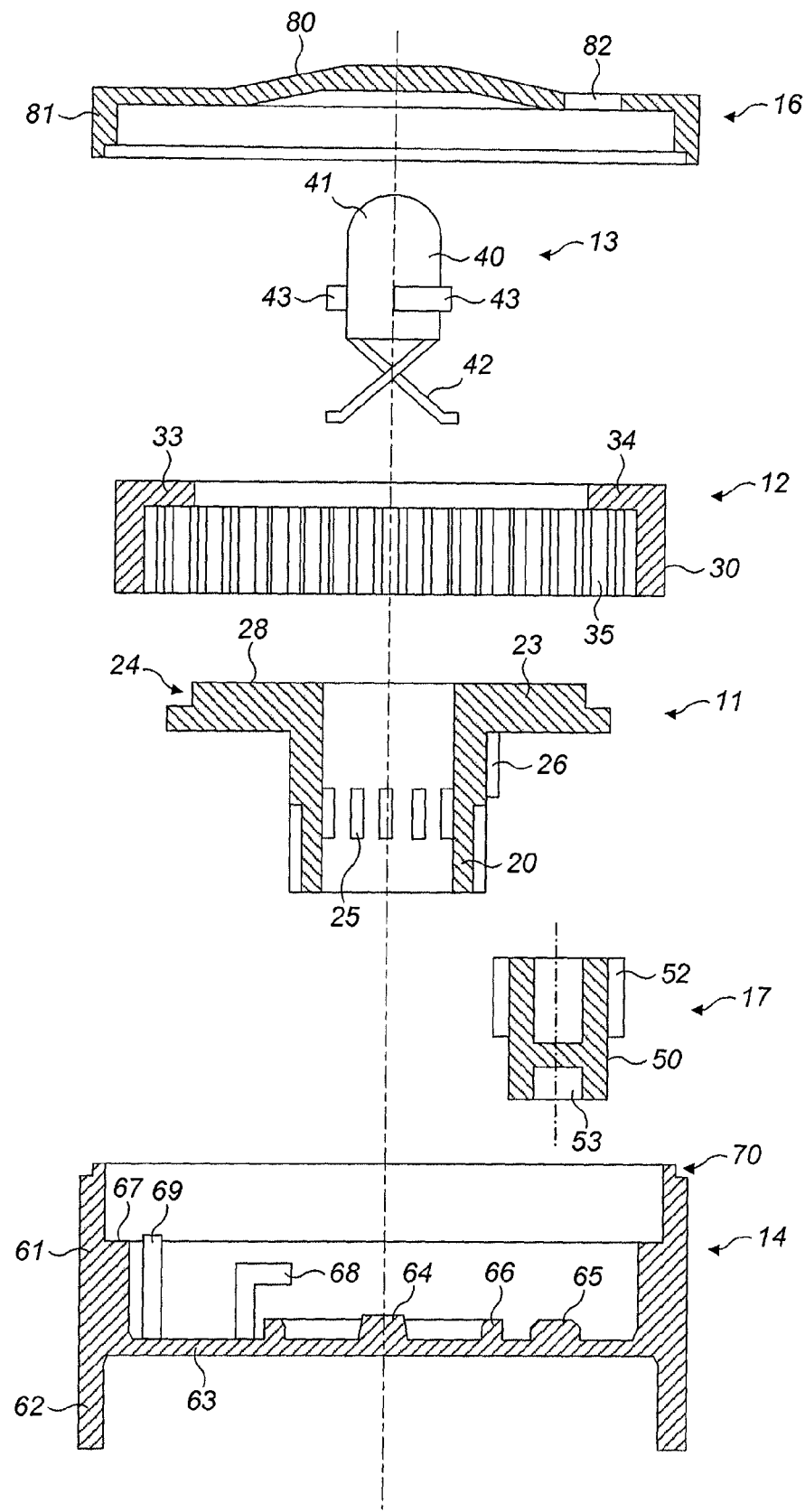
FIG. 5 is an exploded part cross-sectional view of the dose indicator device of FIG. 4.

A second embodiment is shown in FIGS. 4 and 5. In this embodiment, the drive member 13 comprises a body 40, a domed head 41, two sprung legs 42 and drive arms 43.

On assembly of the dosage indicator device the domed head 41 is in contact with the underside of the flexible plate 80 of the flexible cover 16 but is not attached thereto. The domed nature of the domed head 41 is so as to reduce friction between the domed head 41 and the underside of the flexible plate 80.

Depression of the flexible plate 80 by the user actuates the metered dose inhaler in the same way as for the first embodiment. However, instead of converting translational movement of the flexible plate 80 with respect to the drive member 13 using a peg and slot arrangement, two sprung legs 42 are used. The sprung legs 42 are such that the body 40 of the drive member 13 rotates as the dome 41 is depressed. Rotational movement of the body 40 is converted to rotational movement of the inner wheel 11 by virtue of drive arms 43 which act in the same manner as for the first embodiment.

Figure 6:
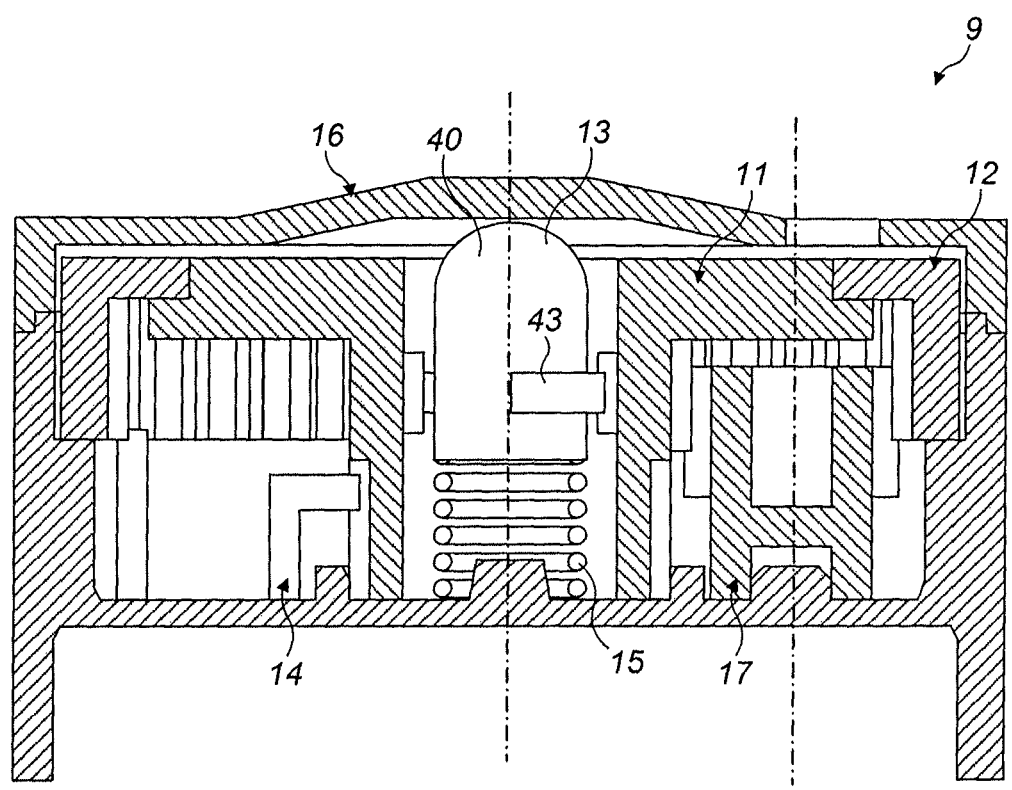
FIG. 6 is a part cross-sectional view of a third embodiment of a dose indicator device according to the present disclosure.

A third embodiment is shown in FIG. 6. This embodiment is the same as the second embodiment except that the two sprung legs 42 are replaced by a helical spring 15 which is connected to the body 40 such that when the body 40 moves downwards, the spring 15 compresses which causes the upper end of the spring 15 to rotate which in turn causes the body 40 to rotate also. Again, the drive arms 43 act in the same manner as for the first and second embodiments.

The invention claimed is:

1. A dose indicator device for a pressurised metered dose inhaler comprising:
 a base suitable for mounting to an upper end of a dispensing container of a pressurised metered dose inhaler, an annular inner wheel, an annular outer wheel, a drive member, a transmission cog and a flexible cover;
 the drive member, annular inner wheel and annular outer wheel being concentrically mounted on the base to be rotatable about a first axis of rotation;
 the transmission cog being mounted on the base between the annular inner wheel and the annular outer wheel to be rotatable about a second axis of rotation parallel to the first axis of rotation;
 the annular inner wheel comprising a plurality of primary indexing teeth on an inner annular surface thereof and one or more secondary indexing teeth on an outer annular surface thereof;

the annular outer wheel comprising a plurality of indexing teeth on an inner annular surface thereof;

the transmission cog comprising a plurality of gear teeth on an outer annular face thereof which, in use, can engage the indexing teeth of the annular outer wheel and which can also be engaged by the one or more secondary indexing teeth of the annular inner wheel;

the drive member being mounted within the annular inner wheel;

the drive member comprising a body having one or more drive arms which, in use, can engage the primary indexing teeth of the annular inner wheel;

the flexible cover being flexible downwardly wherein, in use, downward movement of the drive member is accompanied by rotation of the drive member about the first axis of rotation; said rotation causing rotation of the annular inner wheel by interengagement of the drive arms of the drive member and the primary indexing teeth of the annular inner wheel.

2. A dose indicator device as claimed in claim 1 wherein the flexible cover and drive member are interconnected such that downward movement of the flexible cover is accompanied by rotation of the drive member about the first axis of rotation.

3. A dose indicator device as claimed in claim 1 wherein the flexible cover comprises, or is coupled to, one part of a cam and follower mechanism and the drive member comprises, or is coupled to, another part of the cam and follower mechanism.

4. A dose indicator device as claimed in claim 3 wherein the follower of the cam and follower mechanism is one or more pegs and the cam of the cam and follower mechanism is a cam surface provided by one or more slots that slidingly receive the one or more pegs.

5. A dose indicator device as claimed in claim 1 wherein the flexible cover has an inherent memory which causes the flexible cover to return to its inherent shape in the absence of a force.

6. A dose indicator device as claimed in claim 1 wherein a lower end of the body of the drive member which contacts a central boss of the base is dome-shaped.

7. A dose indicator device as claimed in claim 1 wherein the drive member comprises a biasing mechanism.

8. A dose indicator device as claimed in claim 7 wherein the biasing mechanism is a coil spring.

9. A dose indicator device as claimed in claim 7 wherein the biasing mechanism comprises a plurality of flexible legs depending from the drive member body which are orientated relative to the first axis of rotation such that movement of the drive member body along the first axis of rotation causes twisting of the drive member body about the first axis of rotation.

10. A dose indicator device as claimed in claim 1 wherein an upper end of the drive member which contacts the flexible cover is dome-shaped.

11. A dose indicator device as claimed in claim 1 wherein the base comprises a first ratchet mechanism engageable with the annular inner wheel and a second ratchet mechanism engageable with the annular outer wheel.

12. A dose indicator device as claimed in claim 1 wherein the annular inner wheel, the transmission cog and the annular outer wheel have a gear ratio such that for every 10 incremental rotations of the annular inner wheel the annular outer wheel is incrementally rotated once.

13. A dose indicator device of claim 1 consisting of six component parts.

14. A dose indicator device of claim 13 wherein each of the component parts is formed from plastics mouldings.

15. A pressurised metered dose inhaler comprising a dose indicator device as claimed in claim 1.

16. A dose indicator device of claim 1 wherein all components of the indicator device are formed from plastics mouldings.

* * * * *